(12) United States Patent
Perez et al.

(10) Patent No.: US 9,888,950 B2
(45) Date of Patent: Feb. 13, 2018

(54) PLATE BENDERS AND SYSTEM

(71) Applicant: Biomet C.V., Gibraltar (GI)

(72) Inventors: Alejandro Perez, Miami, FL (US);
Priya Prasad, Sunrise, FL (US);
Driany F. Alfonso, Surfside, FL (US);
Sanjoy Chouduri, Kolkata (IN)

(73) Assignee: Biomet C.V., Warsaw, IN (US)

( * ) Notice: Subject to any disclaimer, the term of this patent is extended or adjusted under 35 U.S.C. 154(b) by 577 days.

(21) Appl. No.: 14/540,926

(22) Filed: Nov. 13, 2014

(65) Prior Publication Data

US 2015/0142064 A1 May 21, 2015

Related U.S. Application Data

(60) Provisional application No. 61/905,323, filed on Nov. 18, 2013.

(51) Int. Cl.
*A61B 17/80* (2006.01)
*A61B 17/88* (2006.01)
*A61B 17/17* (2006.01)

(52) U.S. Cl.
CPC ...... *A61B 17/8085* (2013.01); *A61B 17/1728* (2013.01); *A61B 17/80* (2013.01); *A61B 17/8061* (2013.01); *A61B 17/8863* (2013.01)

(58) Field of Classification Search
CPC .................. A61B 17/8085; A61B 17/8863
See application file for complete search history.

(56) References Cited

U.S. PATENT DOCUMENTS

| | | | |
|---|---|---|---|
| 7,935,126 B2 | 5/2011 | Orbay et al. | |
| 8,568,462 B2 | 10/2013 | Sixto, Jr. et al. | |
| 2012/0065689 A1 | 3/2012 | Prasad et al. | |
| 2015/0289918 A1* | 10/2015 | Burckhardt | A61B 17/8863 264/339 |

OTHER PUBLICATIONS

Product Rationale & Surgical Technique, Alps Total Foot System, Biomet Orthopedics, 2012.

* cited by examiner

*Primary Examiner* — Andrew Yang
(74) *Attorney, Agent, or Firm* — Schwegman Lundberg & Woessner, P.A.

(57) ABSTRACT

A pair of plate benders is provided for bending a bone plate having a plurality of screw holes and a plurality of tubular drill guides removably preassembled into the screw holes. Each plate bender has a first end, a second end, and a handle extending between the first and second ends. The first end has a lower table on which the plate is received, an upper retaining structure which is adapted to engage the tubular drill guides, a recess defined between the lower table and upper retaining structure into which a portion of the plate is received such that the plate extends over a portion of the table and below a portion of the retaining structure. The retaining structure engages the periphery of the tubular drill guides to secure the plate relative to the bending tool.

20 Claims, 9 Drawing Sheets

PLATE BENDERS AND SYSTEM

CROSS-REFERENCE TO RELATED APPLICATION

This application claims benefit of U.S. Provisional Application No. 61/905,323, filed, Nov. 18, 2013, which is hereby incorporated by reference herein in its entirety.

BACKGROUND OF THE INVENTION

1. Field of the Invention

The present disclosure relates to plates and bending tools to reshape the plates. More particularly, the present disclosure relates to plates suitable for use in fusing the proximal and distal joints of the metatarsal bone, and plate benders for reshaping these and other plates.

2. State of the Art

Plating systems for treating the bones of the foot are known. By way of example, the A.L.P.S. Total Foot System from Biomet includes the several plates and screw types required to stabilize the bones and joints of a foot, depending on the procedure performed and the surgeon's prescription.

SUMMARY OF THE INVENTION

Plates are provided for fusing proximal and distal metatarsal joints. A first fusion plate is provided for placement on the 1st metatarsal to fuse the relatively proximal metatarsal-cuneiform (MTC) joint. The first fusion plate is structured to provide high torsional rigidity relative to other podiatric single joint fusion plates. The first fusion plate specifically has a double bridge configuration extending in the longitudinal direction for high stability and contourability over the joint. The plate has a plurality of threaded holes, particularly at the ends of the double bridge configuration, that threadedly receive short tubular guides of the type described in detail in U.S. Pat. Nos. 7,935,126 and 8,568,462. Generally, the guides have a tubular body, an axial bore through the body of a diameter and length for stably guiding a drill, an internal non-cylindrical tool engagement feature within the bore at the proximal end of the body for engagement with a tool for applying a rotational force for removal of the drill guide from the threaded hole, and a threaded portion extending distally from the distal end of the body for engagement with the threaded holes. The guides are preferably removably preassembled into respective ones of the threaded holes. The first fusion plate also includes a dynamic compression hole that allows for 1.25 mm of MTC joint compression.

A second fusion plate is provided for placement on the 1st metatarsal to fuse the relatively distal metatarsal phalangeal (MTP) joint. The second fusion plate is provided in multiple sizes, accommodating patients with larger and smaller bones. The second fusion plate is similar to the plate described in US Pub. No. 20120065689, which is hereby incorporated by reference herein in its entirety. The plate has six threaded holes, arranged in two groups of three at each end of the plate into which is threadedly received short tubular guides of the type described above. The second fusion plate has a central hole separating the two groups of three holes to allow the insertion and capture of bone graft material, e.g., in the event the metatarsal is lengthened at the joint site. In general, the 1st MTP joint is fused at an average of 7 degrees of dorsiflexion and 5 degrees vagus, but it is recognized that the angle may vary from patient to patient. The second fusion plate is bendable to allow the second plate to match the appropriate angle of fusion.

In accord with another aspect of disclosure, a plate bender is provided for bending the second fusion plate in dorsiflexion. The plate bender is preferably provided as a matching pair of two like plate benders. Generally, the bender defines a recess between upper and lower structures in which a portion of the plate is received, and the bender includes structure that contacts and engages the outer periphery of at least some and preferably all of the tubular guides. In one embodiment, one tubular guide at the end of the plate portion is captured within a curved slot, and another tubular guide closest to a fulcrum of the bender is captured within a straight slot. The slots are sized to closely accommodate the diameter of the tubular guides for purposes of stability.

More specifically, each plate bender includes a first end, a second end, and a lever arm therebetween. Each end is preferably distinguished only in size so that the first end is adapted to accommodate a plate of a different size than the second end is adapted to accommodate. The first end has two sides, with structure having lateral mirror symmetry about the longitudinal axis of the lever arm. With reference to one side at the first end, the bender includes a table, a guide retaining structure displaced from the table, a recessed space provided between the table and the retaining structure for receiving a portion of the plate. The retaining structure includes a crook, a slot extending into the crook, a catch at the end of the slot and defined by and within the crook, a straight slot, and a stabilizing wall between the straight slot and crook. Distalmost upper and lower fulcrums are also provided.

In use, the second fusion plate is provided with two sets of three tubular guides threadedly attached thereto, as described above. The first set of guides is a distal set in the 'as implanted' configuration, while the second set of guides is the proximal set in the 'as implanted' configuration. The plate is positioned into the recessed space with the distalmost or first guide (of the 'as implanted' configuration) of the first set of guides pushed into the curved slot. The plate is then rotated and pulled distally relative to the bender so that (i) the first guide of the first set is advanced through the slot to the catch such that crook cups and captures the guide, (ii) the proximalmost or third guide (of the implanted configuration) of the first set is received in the straight slot, and (iii) the central or second guide of the first set is abutted against the stabilizing wall. In accord with a preferred aspect of the bender, the width of the crook is sized to fit closely between the first and second guides so as to guide rotation of the plate as it is rotated between the two positions. The slots are sized to closely receive the first and third guides. The locations of the slots and wall, and size of the slots are preferably designed to provide maximum stabilization to the fusion plate when it extends substantially parallel to the axis of the lever arm with a substantial second portion thereof extending beyond the fulcrum.

Then, a second plate bender is attached to the free end of the second portion of the second fusion plate. More specifically, the plate is positioned into the recessed space thereof, with the first guide of the second set of guides (now the proximalmost guide in the 'as implanted' configuration) inserted into the curved slot. The second bender is then rotated relative to the free end of second fusion plate to stabilize the first, second and third guides of the second set relative to the curved slot, the stabilizing wall, and the straight slot, respectively. It is recognized that the capture of the second portion of the plate may not be as secure as the first portion. However, the plate is sufficiently retained such that it will not become dislodged during application of force in the intended direction. Once the plate is capture by the benders, force may be applied to subject the plate to a change of angle in dorsiflexion, i.e., to either increase or decrease the angle.

DETAILED DESCRIPTION OF THE PREFERRED EMBODIMENTS

With reference to the human body and components of the system described herein which are intended to be implanted in the human body, the terms "proximal" and "distal" are defined in reference to the location at which a limb is connected to the torso, with the term "proximal" being the end of the limb, bone, or plate closer to the torso, and the term "distal" being the end of the limb, bone, or plate further from the torso. In addition, the term "lower" and "upper" in reference to plate surfaces are designations in which the lower surface is that surface closer to or seating on the bone, and the upper surface is that surface opposite the lower surface. Further, with respect to a plate, the terms "length", "width" and "thickness" are relatively transverse dimensions with the length being the dimension along the longitudinal axis of a plate, the width is a laterally transverse dimension to the length, and the thickness is a dimension extending between the upper and lower surfaces of the plate.

With reference to instruments of the system that are hand-held by a user, such as a plate bender, the terms "proximal" and "distal" are defined in reference to the user's hand, with the term "proximal" being closer to the user's hand, and the term "distal" being further from the user's hand.

Figure 1:
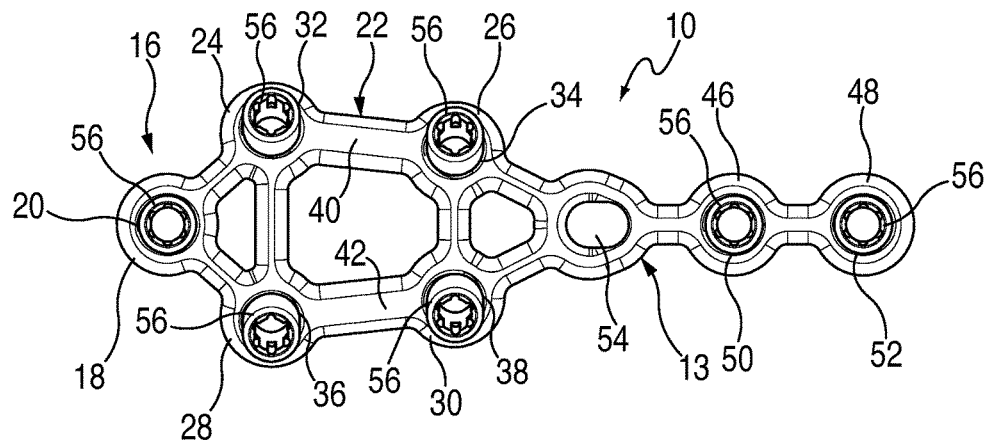
FIG. 1 is a top view of a fusion plate for placement on the 1st metatarsal to fuse the metatarsal-cuneiform (MTC) joint, shown with tubular guides threadedly engaged at each of a plurality of threaded fixed angle holes.
Figure 2:
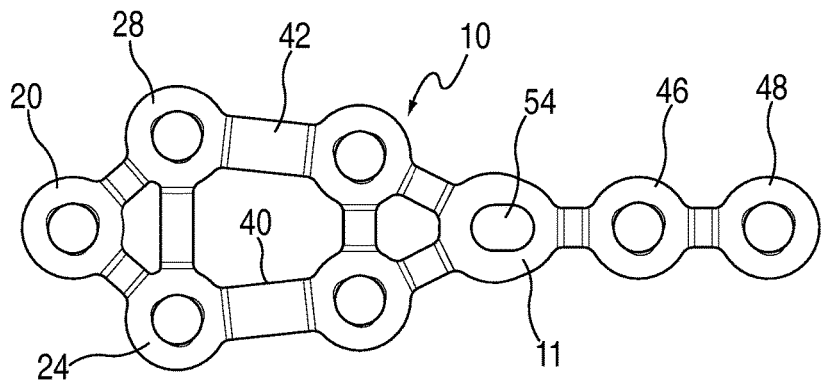
FIG. 2 is a bottom view of the fusion plate of FIG. 1.
Figure 3:
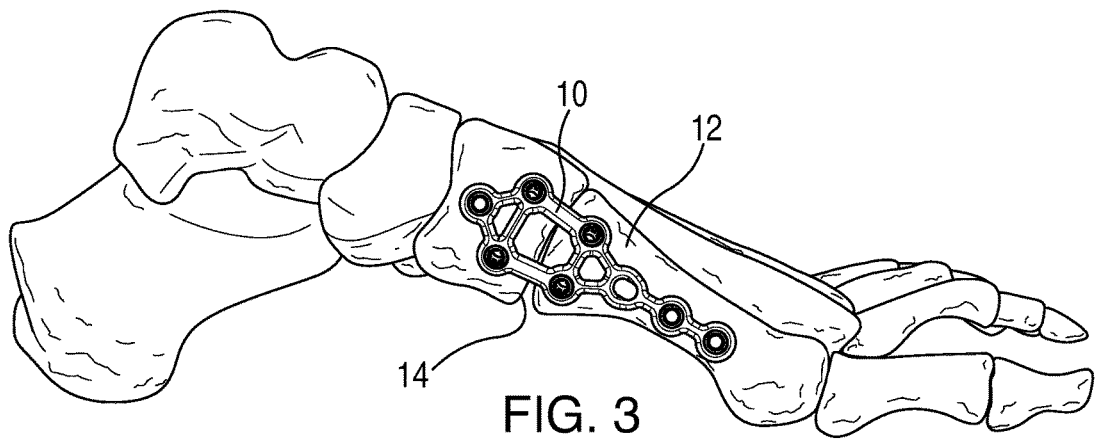
FIG. 3 is an illustration of the plate of FIGS. 1 and 2 shown implanted on the 1st metatarsal to fuse the MTC joint.

Fusion plates are provided for fusing proximal and distal joints of the 1st metatarsal. Referring now to FIGS. 1 through 3, a first fusion plate 10 is provided for placement on the 1st metatarsal 12 to fuse the relatively proximal metatarsal-cuneiform (MTC) joint 14, e.g., in a lapidus procedure. The first fusion plate 10 is structured to provide high torsional rigidity relative to other podiatric single joint fusion plates. The first fusion plate 10 has a bone contacting first surface 11, an opposite second surface 13, and a plurality of screw holes, defined below, extending between the first and second surfaces. The plate 10 has a proximal end 16 provided with a single node 18 defining a threaded hole 20. Adjacent the proximal node 18, a double bridge 22 extends, with nodes 24, 26, 28, 30 defining threaded holes 32, 34, 36, 38 at each of the ends of the bridge struts 40, 42. Threaded holes are adapted to receive fixed angle threaded-head fixation screws (not shown). The distal end 44 of the first fusion plate 10 defines an axial arrangement of two nodes 46, 48, each defining a threaded hole 50, 52. The nodes 24, 26, 28, 30 on the double bridge 22 provide additional and superior fixation when fusing the MTC joint 14 of the 1st metatarsal 12, while offering maximum stability and contourability over the MTC joint. Between the distal axial holes and the double bridge is located a dynamic compression hole 54 that allows for 1.25 mm of compression of the MTC joint 14.

Figure 7:
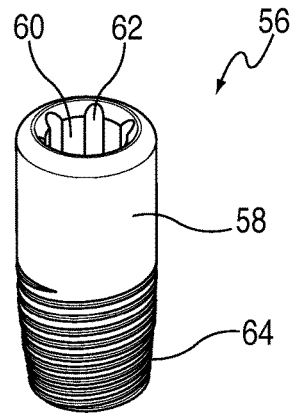
FIG. 7 is a perspective view of a tubular drill guide shown preassembled on the fusion plates.
Figure 8:
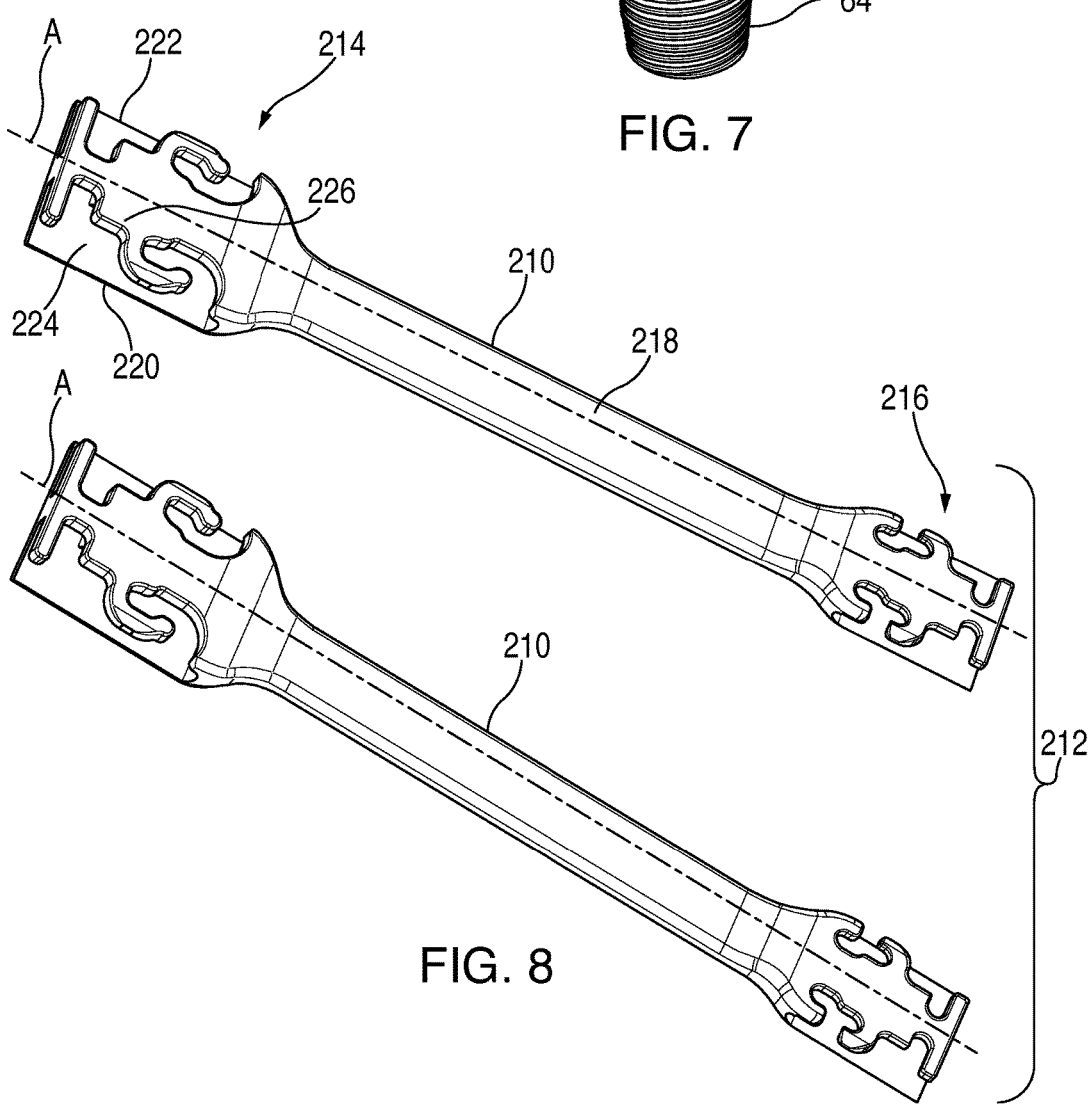
FIG. 8 is a perspective view of a pair of plate benders for bending fusion plate of FIGS. 4 and 5.
Figure 9:
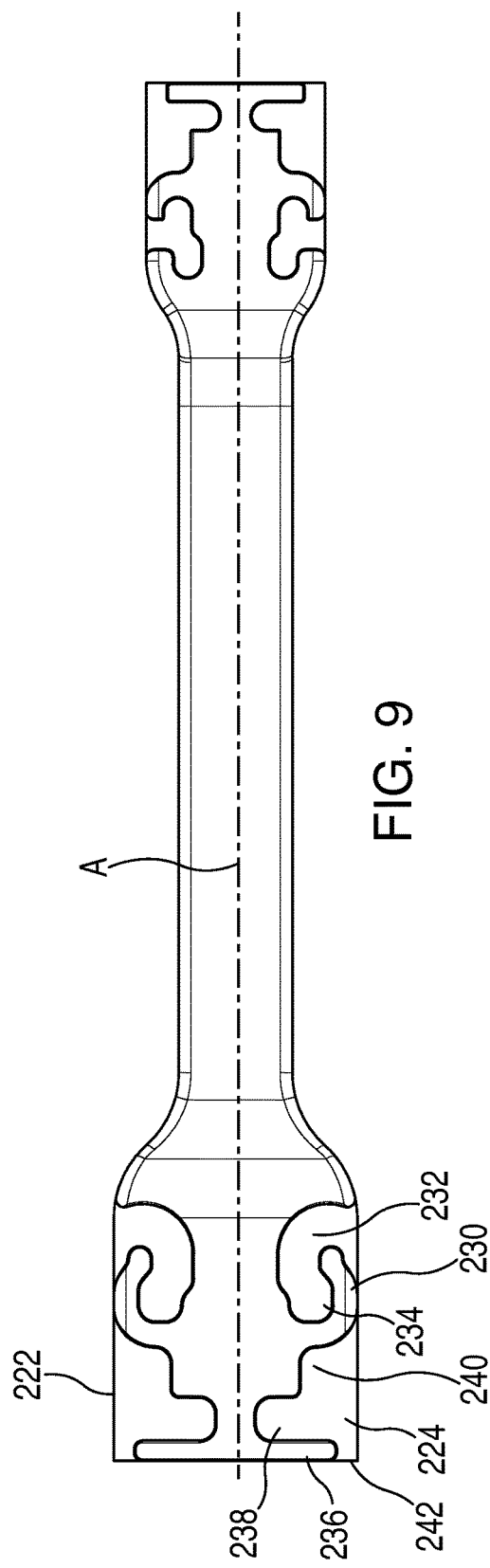
FIG. 9 is a top view of one of the plate benders of FIG. 8.
Figure 10:
FIG. 10 is a side elevation view of the plate bender of FIG. 9.
Figure 11:
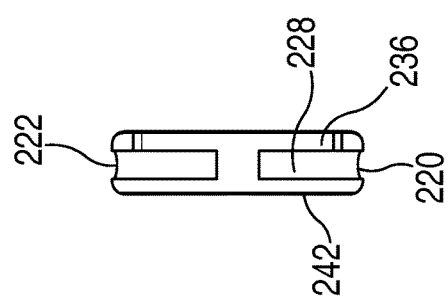
FIG. 11 is an end view of the plate bender of FIG. 9.

In each of the threaded holes of the first fusion plate 10, a short tubular drill guide 56 is threadedly received, preferably preassembled when the plate 10 is received in an implant-ready condition. The tubular guides 56 are preferably of the type described in detail in U.S. Pat. Nos. 7,935,126 and 8,568,462, which are hereby incorporated by reference herein in their entireties. Referring to FIG. 7, specifically, the tubular guides 56 have a tubular body 58, an axial bore 60 extending through the body of a diameter and length for stably guiding a drill, an internal non-cylindrical tool engagement feature 62 within the bore at the proximal end of the body for engagement with a tool for applying a rotational force for removal of the drill guide from the threaded hole, and a distal threaded portion 64 that engages with the threaded holes.

Figure 4:
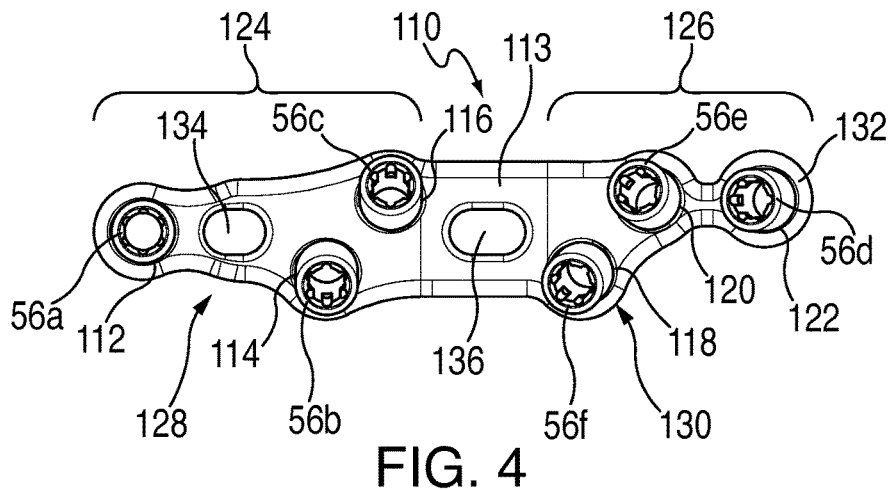
FIG. 4 is a top view of a fusion plate for placement on the left 1st metatarsal to fuse the metatarsal-phalangeal (MTP) joint, shown with tubular guides threadedly engaged at each of a plurality of threaded fixed angle holes.
Figure 5:
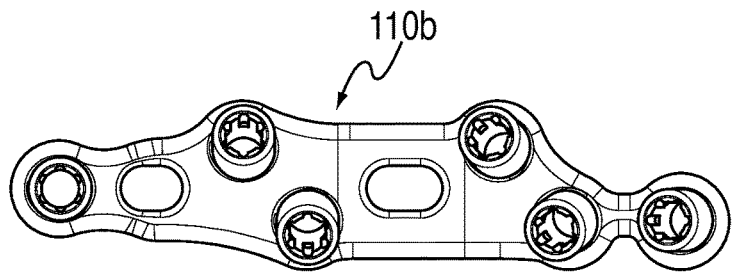
FIG. 5 is a top view of a similar plate with threaded guides to that shown in FIG. 4, adapted for the right 1st metatarsal.
Figure 6:
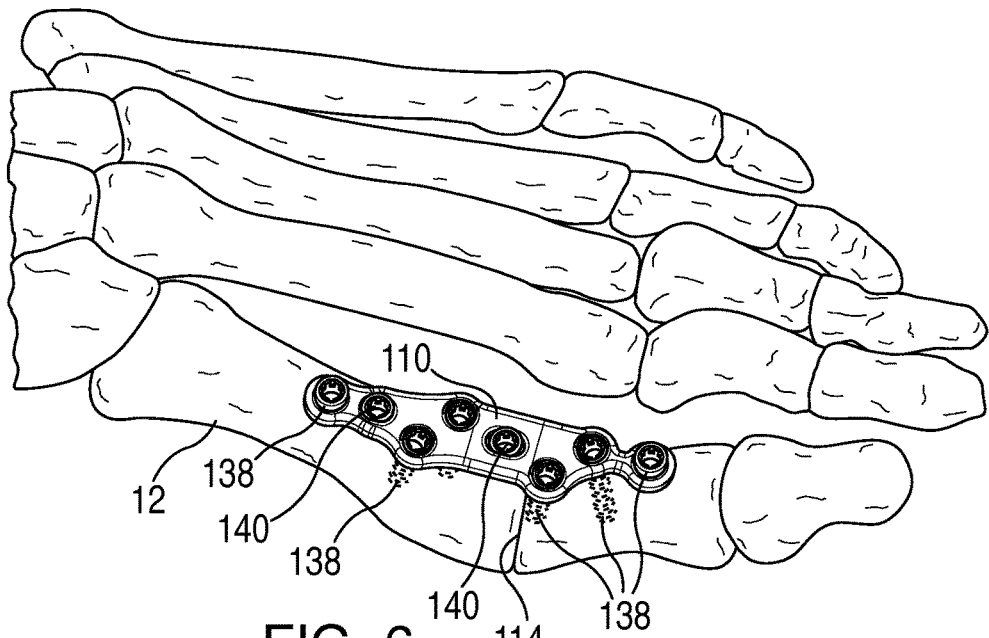
FIG. 6 is an illustration of the plate of FIG. 4 shown implanted on the 1st metatarsal to fuse the MTP joint.

Turning now to FIGS. 4 though 6, a second fusion plate 110 (110 shown for left foot implantation, 110b shown for right foot implantation) is provided for placement on the 1st metatarsal 12 to fuse the relatively distal metatarsal phalangeal (MTP) joint 114. The second fusion plate 110 is provided in multiple sizes, accommodating patients with larger and smaller bones. The second fusion plate is similar to the plate described in US Pub. No. 20120065689, which is hereby incorporated by reference herein in its entirety, but has certain distinctions that are set out below. The plate, with upper second surface 113 shown (and opposite first surface hidden below the plate), has six longitudinally displaced threaded holes 112, 114, 116, 118, 120, 122, arranged in two sets 124, 126 of three each, within respective proximal and distal portions of the plate 128, 130. The distalmost threaded hole 122 is preferably provided within a reconfigurable node 132. The threaded holes threadedly receive short tubular guides 56 of the type described above. Once the threaded guides are removed, the threaded holes are adapted to receive fixed angle screws 138, but may also receive specifically adapted compression screws. A non-threaded compression hole 134 is positioned distally adjacent the proximalmost threaded hole 112 of the first group 124 of threaded holes for receiving a compression screw 140. Plate 110 has a central hole 136 separating the two groups 124, 126 of three holes to allow for the insertion and capture of bone graft material, e.g., in the event the 1st metatarsal 12 is lengthened at the MTP joint 114. The central hole 136 also accommodates a compression screw 140 for optional fixation. In general, the 1st MTP joint 114 is fused at an average of 7 degrees of dorsiflexion and 5 degrees vagus, but it is recognized that the angle may vary from patient to patient. The second fusion plate 110 is bendable under appropriate force and with appropriate tools to match or otherwise correspond to an appropriate angle of fusion.

Turning now to FIGS. 7 through 11, in accord with another aspect of disclosure, plate benders 210 are provided for applying force at an appropriate location to bend the second fusion plate 110 (FIG. 4) in dorsiflexion. The plate benders are preferably provided as a matching pair 212 of two like plate benders. Each plate bender 210 includes a first end 214, a second end 216, and a preferably straight lever arm in the form of handle 218 extending therebetween. Each end 214, 216 is preferably distinguished only in size so that the first end is adapted to accommodate a fusion plate of a different size than the second end is adapted to accommodate. The first end 214 has two sides 220, 222, with structure on each side having mirrored lateral symmetry about the longitudinal axis A of the handle 218, which allows the bender to accommodate both left and right side plates 110, 110*b*, as well as attachment to either end of the plate 110, as discussed below.

With reference to one side 220, the bender includes a table 224, retaining structure 226 displaced from the table 224, and a recessed space 228 defined between the table 224 and the retaining structure 226 for receiving a portion of the plate 110. The retaining structure 226 includes a crook 230, a curved slot 232 extending into the crook, a terminus or catch 234 at the end of the slot and defined by and within the crook, a distal upper fulcrum in the form of bar 236, a short straight slot 238 adjacent the bar 236 and extending orthogonally to the longitudinal axis A, and a stabilizing wall 240 defined between the crook 230 and the straight slot 238. A distal lower fulcrum is provided in the form of the distalmost end 242 of the table 224.

Figure 12:
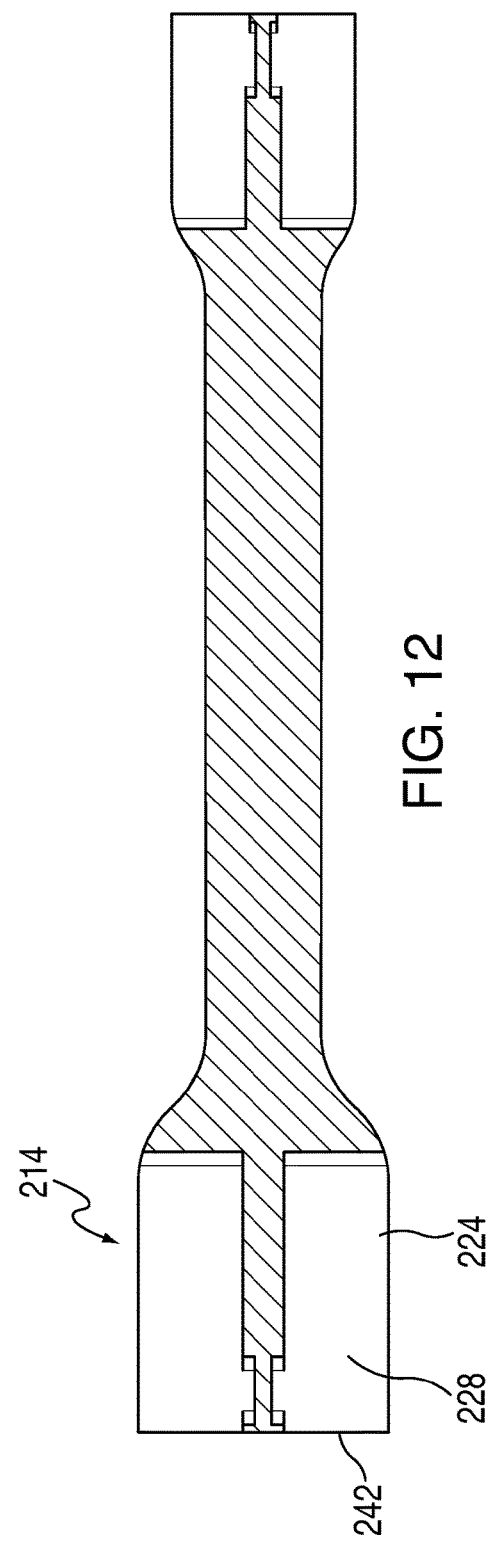
FIG. 12 is a longitudinal section view of the plate bender of FIG. 9, with the section taken across line 12-12 in FIG. 10.
Figure 13:
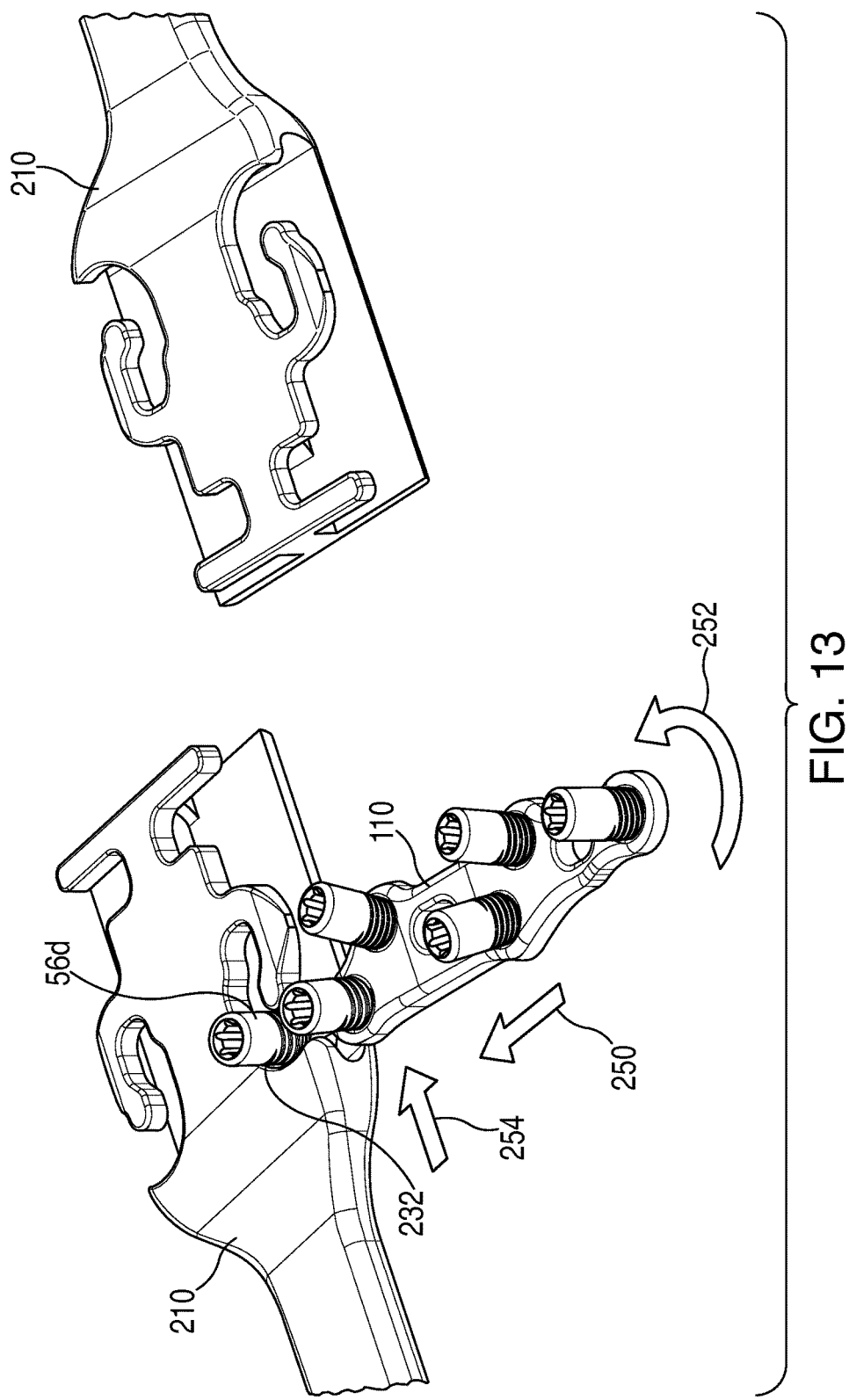
FIGS. 13 through 16 illustrate use of the pair of the plate benders of FIG. 8 to bend and change the angle of dorsiflexion of the fusion plate of FIG. 4.

In use, the second fusion plate 110 is provided with two sets of three tubular guides 56*a-f* threadedly attached thereto at the threaded holes, as described above. The first set 124 of guides 56*a*, 56*b*, 56*c* is the proximal set in the 'as implanted' configuration, while the second set 126 of guides 56*d*, 56*e*, 56*f* is the distal set in the 'as implanted' configuration. Referring to FIG. 13, the distal portion of the plate 110 is attached to a first of the plate benders, with a portion thereof positioned into the recessed space 228 (see FIGS. 10-12). With the plate oriented transverse to the axis A of the bender, the distalmost or first guide 56*d* (at node 132) of the second set 126 of guides is pushed into the entry of the curved slot 232, as shown by arrow 250. The plate 210 is then rotated, in the direction of arrow 252, and pulled distally relative to the bender 210, in the direction of arrow 254, so that (i) the first guide 56*d* of the second set is advanced through the curved slot 232 and into the catch 234 such that crook 230 cups and captures the outside of the first guide 56*d*, (ii) the proximalmost or third guide 56*f* (of the 'as implanted' configuration) of the second set 126 of guides is rotated into engagement into the straight slot 238, and (iii) the central or second guide 56*e* of the second set is received into abutment against the stabilizing wall 240. It should be appreciated that the table 224 extends under the first portion of the plate, and the crook 230 and the bar 236 extend over the first portion of the plate. With the plate 110 and guides 56*d*, 56*e*, 56*f* of the second set 126 thusly oriented relative to each other, the plate is locked relative to the plate bender.

In accord with a preferred aspect of the bender, the width of the arm of the crook 230 is preferably sized to fit closely between the first and second guides 56*d* and 56*e* so as to guide rotation of the plate 110 as it is rotated between the unlocked and locked positions. In addition, the straight slot 238 is sized in width to closely receive the diameter of the third guide 56*f*. The locations of the straight slot 238 and stabilizing wall 240, and the size of the straight slot are preferably designed to provide maximum stabilization to the fusion plate 110 when it extends substantially parallel to the axis A of the lever arm handle 218. Once a first portion 244 is locked relative to the first bender, a substantial second portion 246 of the plate 110 extends beyond the distal end of the first bender 210.

Figure 14:
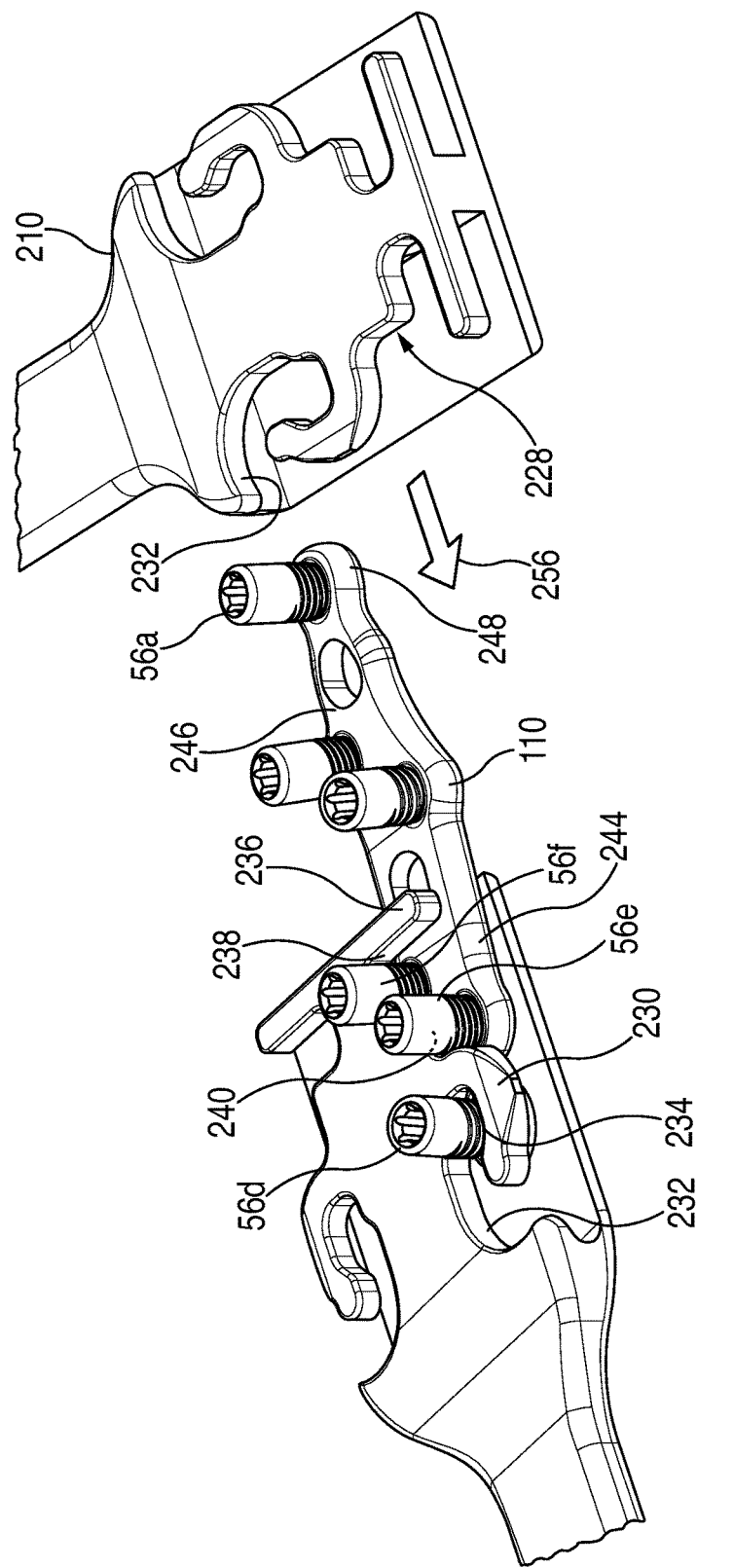
Figure 15:
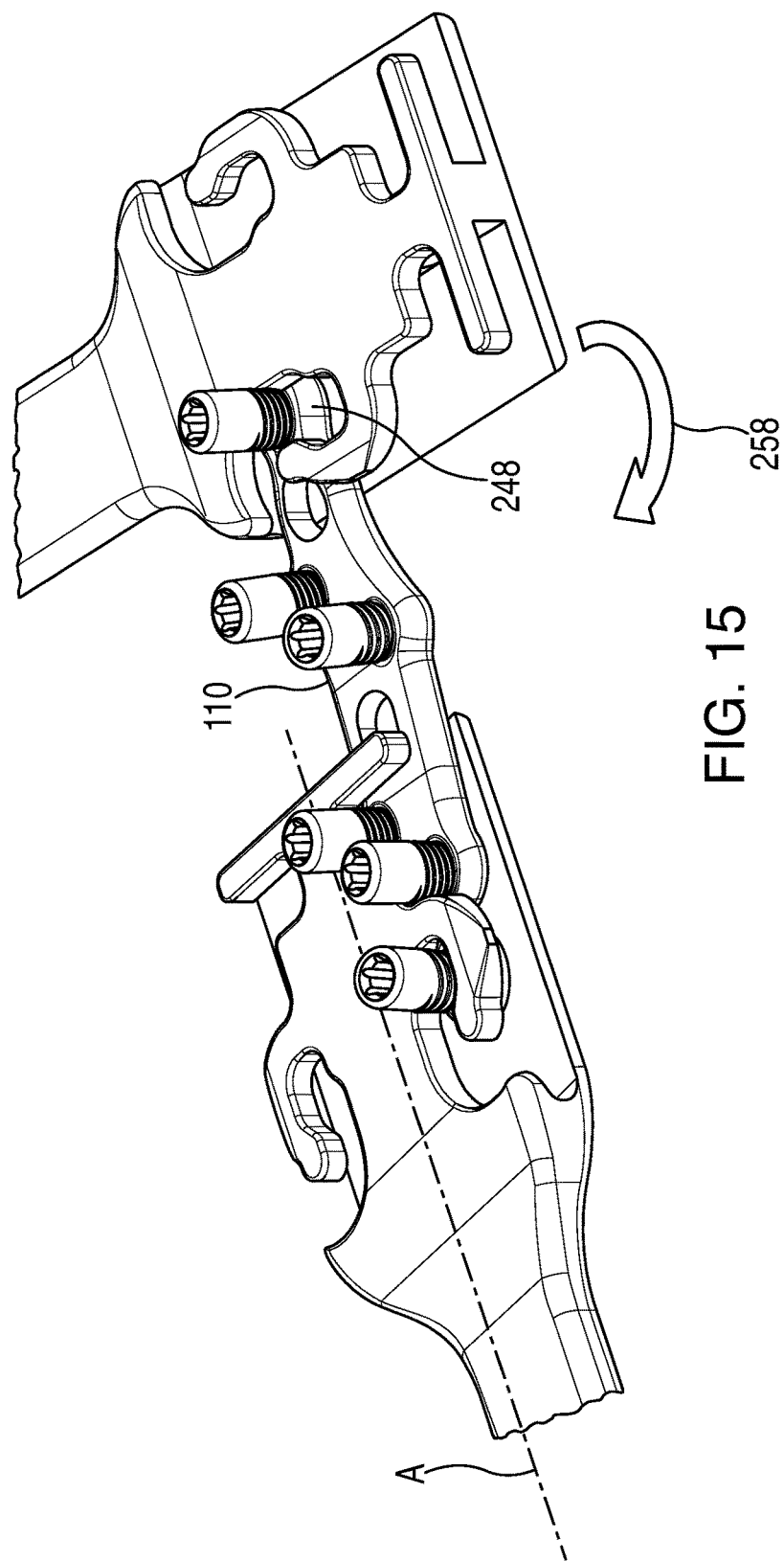
Figure 16:
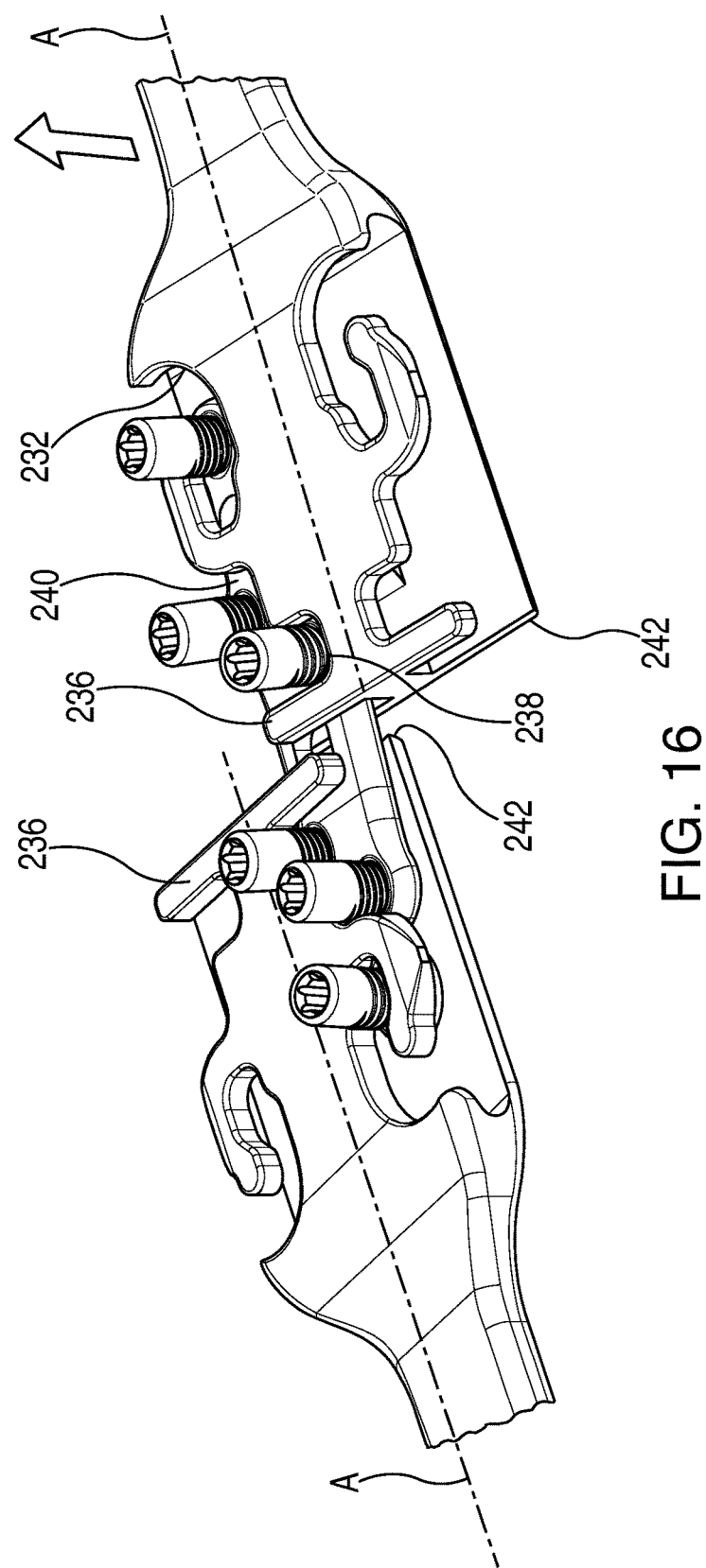

Then, referring to FIG. 14, a second plate bender 210 is attached to the free end 248 of the second portion 246 of the fusion plate 110 in the direction of arrow 256. More specifically, the second bender is positioned on the second portion 246 such that the recessed space 228 receives the second (proximal) portion, and the first guide 56*a* of the first set 124 of guides (the proximalmost guide in the 'as implanted' configuration) is advanced into the curved slot 232. Then the second bender 210 is rotated in the direction of arrow 258 relative to the free end 248 of fusion plate 110 from the orientation shown in FIG. 15 (transverse to the longitudinal axis A of the first bender) into the configuration shown in FIG. 16 (such that the longitudinal axes A of each of the first and second benders are substantially parallel (within 5° thereof) to stabilize the first 56*a*, second 56*b* and third guides 56*c* of the first set 124 relative to the curved slot 232, the stabilizing wall 240, and the straight slot 238, respectively. Due to the configuration of the tubular guides 56 in the particular plate 110, which is not laterally symmetrical, and the use of laterally symmetric benders, it is recognized that the retention of the second portion of the plate may not be as secure as the retention of the first portion. However, the plate is sufficiently retained in the second bender such that it will not slide out during application of force in the intended directions. Once the plate is capture by the pair of benders, force may be applied to the lever arm handles 218 to apply a deformation force between the respective upper or lower fulcrums 236, 242 of the benders and thereby subject the plate to a change of angle in dorsiflexion, i.e., to either increase or decrease the angle, depending on the direction in which the force is applied. That is, the angle can be increased by applying a bending force about upper fulcrums 236, and the angle can be decreased by applying a bending force about lower fulcrums 242.

It is appreciated that while one order of coupling a pair of plate benders to the first and second portions of the fusion plate is described, it is appreciated that the plate benders may be coupled in a different order. For example, a first plate bender may be first coupled to the second (proximal) portion of the fusion plate, and second plate bender then may be coupled to the first (distal) portion of the fusion plate. That is, the operations shown and described with respect to FIG. 15 may be effected prior to the operations shown in FIG. 13.

From the above, it is seen that each plate bender retains a portion of the fusion plate by capturing such portion within a recess between the respective upper and lower structures that sandwiches the lower bone contacting surface and opposite upper surface of the fusion plate. In addition, the bender contacts and engages the outer periphery of at least some and preferably all of the tubular guides, without engaging over the top of the tubular guides. Specifically, one tubular guide at the end of the plate portion is captured within a curved slot, and another tubular guide closest to the fulcrum is captured within a straight slot. Each slot is sized to closely accommodate the diameter of the tubular guide to provide sufficient securement between the bender and guide, and thus the plate, to effect attachment of the bender to the plate to facilitate plate bending.

There have been described and illustrated herein several embodiments of a fusion plate for providing additional fixation to the metatarsal and metatarsal phalangeal joints, and plate benders that can be used to reshape the plates, as well as methods of using the benders to reshape the plates. It is recognized that benders, of potentially different size but similar structure, or of different structure but similar operation and/or effect, can be used to reshape other bone plates used at different locations in the body. It will therefore be appreciated by those skilled in the art that yet other modifications could be made to the provided invention without deviating from its scope.

What is claimed is:

1. A plate bending tool for use with a plate having a bone contacting first surface, an opposite second surface, a plurality of screw holes extending between the first and second surfaces, and a plurality of tubular drill guides removably preassembled into the screw holes, the bending tool comprising:
    a) a first end having a lower table on which the first surface of the plate is received, an upper retaining structure which is adapted to engage the tubular drill guides, and a recess defined between the lower table and the upper retaining structure, wherein when the plate extends over a portion of the table and below a portion of the retaining structure and the retaining structure engages the tubular drill guides to secure the plate relative to the bending tool, wherein the retaining structure includes a first slot, a second slot and a wall between the first and the second slots, wherein the first and second slots are sized to accommodate simultaneously receiving the tubular drill guides;
    b) a second end; and
    c) a handle extending between the first and second ends.

2. A bending tool according to claim 1, wherein: the handle defines a longitudinal axis, and the first end has lateral mirror symmetry relative to the longitudinal axis.

3. A bending tool according to claim 1, wherein: the second end has like structure to the first end, but provided in a different size.

4. A bending tool according to claim 1, wherein: the first end includes fulcrum located at a distal end thereof.

5. A bending tool according to claim 1, wherein: the first end includes a fulcrum elevated relative to the table and over the recess such that the fulcrum is movably extendable over the second surface of the bone plate and adapted for contact against at least one of the plurality of tubular drill guides.

6. A bending tool according to claim 1, wherein: the first end includes upper and lower fulcrums located at a distalmost end of the first end, the upper and lower fulcrums located above and below the recess.

7. A bending tool according to claim 1 in combination with a second bending tool to comprise a pair of like plate bending tools.

8. A system for bending bone plates, comprising:
    a) a bone plate having a bone contacting first surface, an opposite second surface, a plurality of screw holes extending between the first and second surfaces, and a plurality of tubular drill guides removably preassembled into the screw holes,
    b) a plate bending tool having,
    a first end having a lower table on which the first surface of the plate is received, an upper retaining structure which is adapted to engage the tubular drill guides, a recess defined between the lower table and upper retaining structure into which a portion of the plate is received such that the plate extends over a portion of the table and below a portion of the retaining structure, wherein the retaining structure engages the periphery of the tubular drill guides to secure the plate relative to the bending tool;
    b) a second end; and
    c) a handle extending between the first and second ends.

9. A system according to claim 8, wherein: the guides are engaged relative to the retaining structure by displacing the plate within the recess.

10. A system according to claim 8, wherein: the guides are engaged relative to the retaining structure by rotating and longitudinal displacing the plate within the recess.

11. A system according to claim 8, wherein: the handle defines a longitudinal axis, and the first end has a lateral mirror symmetry relative to the longitudinal axis.

12. A system according to claim 8, wherein: the second end has like structure to the first end, but provided in a different size.

13. A system according to claim 8, wherein: the retaining structure includes a curved slot, a straight slot and a stabilizing wall between the curved and straight slots, wherein the curved and straight slots are sized to closely receive the tubular guides.

14. A system according to claim 8, wherein: the first end includes fulcrum located at a distalmost end thereof.

15. A system according to claim 8, wherein: the first end of the bending tool includes upper and lower fulcrums located at a distalmost end of the first end of the bending tool, the upper and lower fulcrums located above and below the recess.

16. A system according to claim 8, further comprising a second plate bending tool the same as the first plate bending tool.

17. A system according to claim 8, wherein: the tubular guides include proximal guiding ends, and the retaining structure engages the periphery of the tubular guides without covering the guiding ends.

18. A system according to claim 8, wherein: the plate is a fusion plate.

19. A system according to claim 8, wherein: the plate is fusion plate for fusing the 1st metatarsalphalangeal joint.

20. A plate bending tool for use with a plate having a bone contacting first surface, an opposite second surface, a plurality of screw holes extending between the first and second surfaces, and a plurality of tubular drill guides removably preassembled into the screw holes, the bending tool comprising:
    a) a first end having a lower table on which the first surface of the plate is received, an upper retaining structure which is adapted to engage the tubular drill guides, and a recess defined between the lower table and the upper retaining structure, wherein when the plate extends over a portion of the table and below a portion of the retaining structure and the retaining structure engages the tubular drill guides to secure the plate relative to the bending tool;
b) a second end; and
c) a handle extending between the first and second ends, wherein:

the retaining structure includes a curved slot, a straight slot and a stabilizing wall between the curved and straight slots, wherein the curved and straight slots are sized to accommodate simultaneously receiving the tubular guides.

* * * * *